US012576200B2

(12) United States Patent
Matsuda et al.

(10) Patent No.: US 12,576,200 B2
(45) Date of Patent: Mar. 17, 2026

(54) MULTILUMEN CATHETER

(71) Applicant: NIPRO CORPORATION, Osaka (JP)

(72) Inventors: Yusuke Matsuda, Osaka (JP); Shota Nakai, Osaka (JP); Takuma Nakamura, Osaka (JP)

(73) Assignee: NIPRO CORPORATION, Osaka (JP)

( * ) Notice: Subject to any disclaimer, the term of this patent is extended or adjusted under 35 U.S.C. 154(b) by 308 days.

(21) Appl. No.: 18/254,434

(22) PCT Filed: Nov. 24, 2021

(86) PCT No.: PCT/JP2021/043011
§ 371 (c)(1),
(2) Date: May 25, 2023

(87) PCT Pub. No.: WO2022/118714
PCT Pub. Date: Jun. 9, 2022

(65) Prior Publication Data
US 2024/0001018 A1 Jan. 4, 2024

(30) Foreign Application Priority Data
Dec. 1, 2020 (JP) ................................. 2020-199649

(51) Int. Cl.
*A61M 1/36* (2006.01)
*A61M 25/00* (2006.01)

(52) U.S. Cl.
CPC ........ *A61M 1/3661* (2014.02); *A61M 25/007* (2013.01); *A61M 2025/0031* (2013.01); *A61M 2025/0037* (2013.01)

(58) Field of Classification Search
CPC .. A61M 2025/0031; A61M 2025/0037; A61M 25/0068; A61M 1/3661;
(Continued)

(56) References Cited

U.S. PATENT DOCUMENTS 4,423,740 A * 1/1984 Castle ...................... A61B 5/03
600/561
4,808,155 A * 2/1989 Mahurkar ......... A61M 25/0068
604/523
(Continued)

FOREIGN PATENT DOCUMENTS

DE 102005051211 A1 5/2007
EP 2168625 A1 3/2010
(Continued)

OTHER PUBLICATIONS

International Search Report in corresponding International Application PCT/JP2021/043011 mailed on Jan. 25, 2022, with English translation.

*Primary Examiner* — Adam Marcetich
(74) *Attorney, Agent, or Firm* — Renner, Otto, Boissselle & Sklar, LLP

(57) ABSTRACT

A multi-lumen catheter includes a body 101 that is formed into a cylindrical shape and extends from a proximal end to a distal end and surrounded by an outer wall 113; an inner space of the body 101 being divided with a partition 114 extending in a longitudinal direction, into a plurality of lumens including a first lumen 111 and a second lumen 112. The second lumen 112 has a second opening plane 122 at its distal end, and the first lumen 111 has a first opening plane 121 at its distal end, the second opening plane 122 being positioned more distally than the first opening plane 121. The outer wall 113 includes a first outer wall portion 115 defining the first lumen 111 and a second outer wall portion 116 defining the second lumen 112, the first outer wall portion 115 having a first lumen slit 123 notching a portion of a distal end of the first outer wall portion 115. The body 101 includes a flexible portion 141 having a lower hardness, the flexible portion 141 including a distal end portion of the
(Continued)

first outer wall portion 115 wherein the first lumen slit 123 is provided.

20 Claims, 12 Drawing Sheets

(58) Field of Classification Search
        CPC .............. A61M 25/003; A61M 25/007; A61M
                1/3659; A61M 25/0026; A61M 1/3653;
                A61M 2025/0073; A61M 25/0074; A61M
                        25/0067; A61M 2025/0188; A61M
                25/001; A61M 25/008; A61M 2202/0413;
                                        A61M 25/0054
        See application file for complete search history.

(56) References Cited

U.S. PATENT DOCUMENTS

| | | | | |
|---|---|---|---|---|
| 5,215,527 | A | * | 6/1993 | Beck ................. A61M 25/0662 |
| | | | | 604/247 |
| 5,554,136 | A | * | 9/1996 | Luther ................ A61M 25/007 |
| | | | | 604/247 |
| 5,807,311 | A | * | 9/1998 | Palestrant ........... A61M 25/003 |
| | | | | 604/537 |
| 5,807,349 | A | * | 9/1998 | Person ............... A61M 25/007 |
| | | | | 604/537 |
| 6,293,958 | B1 | * | 9/2001 | Berry ............... A61M 25/0075 |
| | | | | 606/191 |
| 6,712,797 | B1 | * | 3/2004 | Southern, Jr. ..... A61M 25/0068 |
| | | | | 604/264 |
| 2003/0144623 | A1 | * | 7/2003 | Heath ............... A61M 25/0023 |
| | | | | 156/60 |
| 2004/0167463 | A1 | * | 8/2004 | Zawacki ............. A61M 1/3653 |
| | | | | 604/43 |

| | | | | |
|---|---|---|---|---|
| 2005/0080430 | A1 | * | 4/2005 | Wright ............... A61B 17/3468 |
| | | | | 606/108 |
| 2006/0004325 | A1 | * | 1/2006 | Hamatake ......... A61M 25/0068 |
| | | | | 604/6.01 |
| 2007/0225682 | A1 | * | 9/2007 | Ash ................... A61M 25/0074 |
| | | | | 604/532 |
| 2009/0187141 | A1 | * | 7/2009 | Lareau ............. A61M 25/0032 |
| | | | | 264/239 |
| 2009/0204052 | A1 | * | 8/2009 | Nimkar ............. A61M 25/0009 |
| | | | | 604/523 |
| 2010/0081986 | A1 | * | 4/2010 | Matson ............. A61M 25/0075 |
| | | | | 604/247 |
| 2011/0054415 | A1 | * | 3/2011 | Onuma ................. A61M 39/22 |
| | | | | 604/247 |
| 2011/0172642 | A1 | * | 7/2011 | Lareau ............. A61M 25/0017 |
| | | | | 604/523 |
| 2013/0046224 | A1 | | 2/2013 | Ravenscroft et al. |
| 2013/0085437 | A1 | * | 4/2013 | Deshpande ......... A61M 1/3661 |
| | | | | 604/246 |
| 2013/0267912 | A1 | * | 10/2013 | Cox ................... A61M 25/0015 |
| | | | | 29/890.12 |
| 2013/0338640 | A1 | * | 12/2013 | Davey ..................... A61M 1/30 |
| | | | | 604/525 |
| 2014/0012209 | A1 | * | 1/2014 | Sansoucy .......... A61M 25/0075 |
| | | | | 604/247 |
| 2018/0056031 | A1 | | 3/2018 | Nardeo |
| 2018/0169382 | A1 | * | 6/2018 | Palko ................ A61M 25/0097 |
| 2018/0207347 | A1 | | 7/2018 | Tal |
| 2020/0069912 | A1 | * | 3/2020 | Tateshima ......... A61M 25/0074 |
| 2020/0269018 | A1 | * | 8/2020 | Khalaj ............. A61M 25/0082 |
| 2021/0268179 | A1 | * | 9/2021 | Schøndorff ........... A61M 25/00 |

FOREIGN PATENT DOCUMENTS

| | | | |
|---|---|---|---|
| EP | | 2574354 A1 | 4/2013 |
| JP | | 2006-15058 A | 1/2006 |
| JP | | 2008-132256 A | 6/2008 |

* cited by examiner

FIG.15
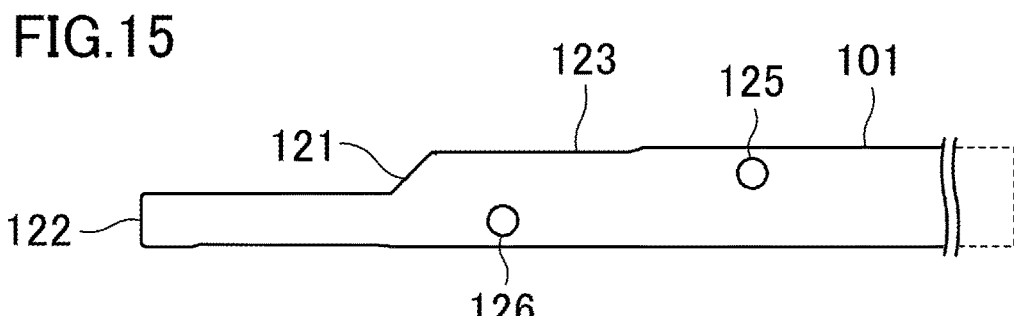
FIG.16
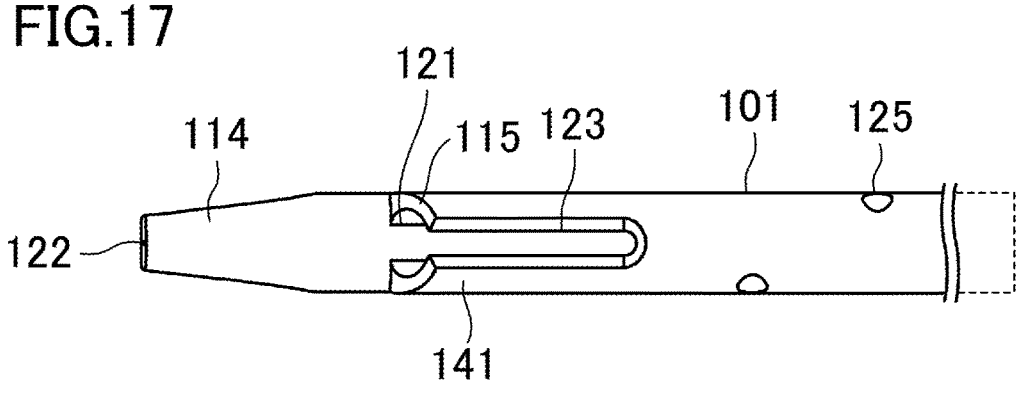
FIG.17
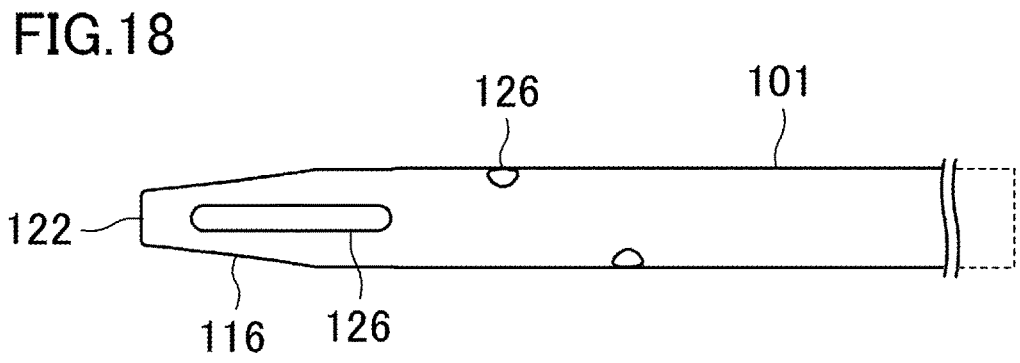
FIG.18

MULTILUMEN CATHETER

This application is a national phase of International Application No. PCT/JP2021/043011 filed Nov. 24, 2021, which claims priority to Japanese Application No. 2020-199649 filed Dec. 1, 2020, each of which is hereby incorporated herein by reference in its entirety.

TECHNICAL FIELD

The present disclosure relates to a multi-lumen catheter.

BACKGROUND ART

In the field of hemodialysis, blood is removed from a blood vessel of a patient and purified outside his/her body, and, thereafter, the purified blood is returned to the blood vessel. In such a case, a multi-lumen catheter is used, which includes at least two lumens, i.e., a blood removal lumen for removing blood from a blood vessel of the patient and a blood return lumen for returning the purified blood into the blood vessel of the patient.

Examples of a method for inserting such a catheter into a blood vessel include a method using an introducer sheath, a method using the Seldinger technique, and the like. In the former method, a catheter is inserted into an introducer sheath which has been inserted into a blood vessel in advance, and the catheter is inserted into the blood vessel along a lumen of the introducer sheath until the catheter reaches a target position. In the latter method, a wire inserted in a blood vessel in advance is inserted in a lumen of the catheter, and the catheter is inserted into the blood vessel along the wire until the catheter reaches a target position.

Some of such lumens of the introducer sheaths include a check valve, so that the catheter insertion into such a lumen of the introducer sheath requires the catheter to be passed through the check valve. Moreover, in the Seldinger technique, in which the catheter is inserted into the blood vessel directly, there is particularly a demand for a catheter with an excellent insertability.

In order to meet such requirements and demands, some conventional catheters are configured as follows: Opening positions of a blood removal lumen and a blood return lumen are disposed at different positions in a longitudinal direction (see Patent Document 1, for example).

CITATION LIST

Patent Document

PATENT DOCUMENT 1: Japanese Unexamined Patent Publication No. 2008-132256

SUMMARY OF THE DISCLOSURE

Technical Problem

The catheter of Patent Document 1 can have a smaller cross-sectional area at the opening position of the blood return lumen at the distal end of the catheter, thereby improving the insertability of a distal end portion of the catheter. On the other hand, there is no change in the cross-sectional area at the opening position of the blood removal lumen, which results in a problem in that insertion resistance of the catheter suddenly increases at this position, so that overall insertability is hardly improved.

It is an object of the present disclosure to realize a multi-lumen catheter with an excellent insertability.

SOLUTIONS TO THE PROBLEMS

An aspect of a catheter according to the present disclosure includes: a body that is formed into a cylindrical shape and extends from a proximal end to a distal end and surrounded by an outer wall, an inner space of the body being divided with a partition extending in a longitudinal direction, into a plurality of lumens including a first lumen and a second lumen, the second lumen having a second opening plane at a distal end thereof, and the first lumen having a first opening plane at a distal end thereof, the second opening plane being positioned more distally than the first opening plane, the outer wall including a first outer wall portion defining the first lumen and a second outer wall portion defining the second lumen, the first outer wall portion having a first lumen slit notching a portion of a distal end of the first outer wall portion, the body including a flexible portion having a lower hardness than other portions of the body, and the flexible portion including a distal end portion of the first outer wall portion where the first lumen slit is provided.

With this configuration, at the catheter insertion, the distal end portion, where the first lumen slit is provided, of the first outer wall portion is deformed to bend into the inner cavity of the first lumen. With this configuration, at the insertion, the cross-sectional area of the body becomes smaller respectively at the first opening plane. Accordingly, the insertion resistance will not increase suddenly, thereby attaining an excellent insertability of the catheter. The distal end portion of the first outer wall portion returns to its original shape after the catheter is indwelled in the blood vessel. This enables to disperse the suction pressure in removing the blood via the first lumen, thereby making it difficult for the sticking to the blood vessel wall to occur.

According to a preferable aspect of the multi-lumen catheter, the first lumen slit may be provided in a circumferential middle portion of the first outer wall portion. This configuration enables to prevent rigidity reduction of the distal end portion of the first outer wall portion while preventing clogging or narrowing of the first opening plane that would be caused by pressing from the blood vessel wall or the like.

According to a preferable aspect of the multi-lumen catheter, the flexible portion may include a portion that ranges from the position of a proximal end of the first lumen slit to the distal end of the body. This configuration allows the catheter to be more easily deformable in such a way that the first outer wall portion bends into the inner cavity of the first lumen, thereby attaining a more gradual change in insertion resistance, which allows for further improvement of the insertability of the catheter. Moreover, this configuration allows the catheter to be less damaging to the blood vessel at the insertion.

According to a preferable aspect of the multi-lumen catheter, the first outer wall portion may have at least one first lumen side pore positioned more proximally than the first lumen slit. This configuration enables to disperse the suction pressure in removing the blood via the first lumen, thereby making it difficult for the sticking to the blood vessel wall to occur. Moreover, this configuration enables to easily ensure the amount of blood removed.

According to a preferable aspect of the multi-lumen catheter, the second outer wall portion may have a second lumen slit notching a portion of a distal end of the second outer wall portion, and the flexible portion may include a distal end portion of the second outer wall portion where the second lumen slit is provided. This configuration enables to make the distal end portion, where the second lumen slit is provided, of the second outer wall portion, deformable to bend into the inner cavity of the second lumen. With this configuration, at the insertion, the cross-sectional area of the body becomes smaller respectively at the second opening plane, thereby further improving the insertability of the catheter. Moreover, the distal end portion of the second outer wall portion returns to its original shape after the catheter is indwelled in the blood vessel, so that the suction pressure can be dispersed in removing the blood via the second lumen, thereby making it difficult for the sticking to the blood vessel wall to occur.

According to a preferable aspect of the multi-lumen catheter, the second outer wall portion may have at least one second lumen side pore. This configuration enables to disperse the suction pressure in removing the blood via the second lumen, thereby making it difficult for the sticking to the blood vessel wall to occur. Moreover, this configuration enables to easily ensure the amount of blood removed.

According to a preferable aspect of the multi-lumen catheter, the first opening plane may be inclined toward the proximal end with respect to the partition, and the second opening plane may be orthogonal to the partition. This configuration enables to obtain a more gradual change in insertion resistance at the first opening plane, thereby further improving the insertability of the catheter. Moreover, this configuration allows for suction pressure reduction at the first opening plane and easily ensures the amount of blood removed.

According to a preferable aspect of the multi-lumen catheter, the plurality of lumens includes three or more lumens. This configuration allows the drug solution administration and the central venous pressure measurement to become performable concurrently with the hemodialysis, thereby reducing the burden on an operator and the patient.

According to a preferable aspect of the multi-lumen catheter, the proximal end of the body is provided with branch pipes being connected respectively to the plurality of lumens and each having a connector at its proximal end. Such a configuration allows hemodialysis to be performed by connecting between the body and a blood circuit and the like via the connectors.

Advantages of the Invention

According to the multi-lumen catheter of the present disclosure, in which the first outer wall portion has the first lumen slit and the flexible portion includes the distal end portion of the first outer wall portion where the first lumen slit is provided, thereby attaining an excellent insertability of the catheter.

BRIEF DESCRIPTION OF THE DRAWINGS

FIG. 15 is a right-side view of the multi-lumen catheter of the fourth variation.

FIG. 16 is a left-side view of the multi-lumen catheter of the fourth variation.

FIG. 17 is a top view of the multi-lumen catheter of the fourth variation.

FIG. 18 is a bottom view of the multi-lumen catheter of the fourth variation.

DESCRIPTION OF EMBODIMENTS

Figure 1:
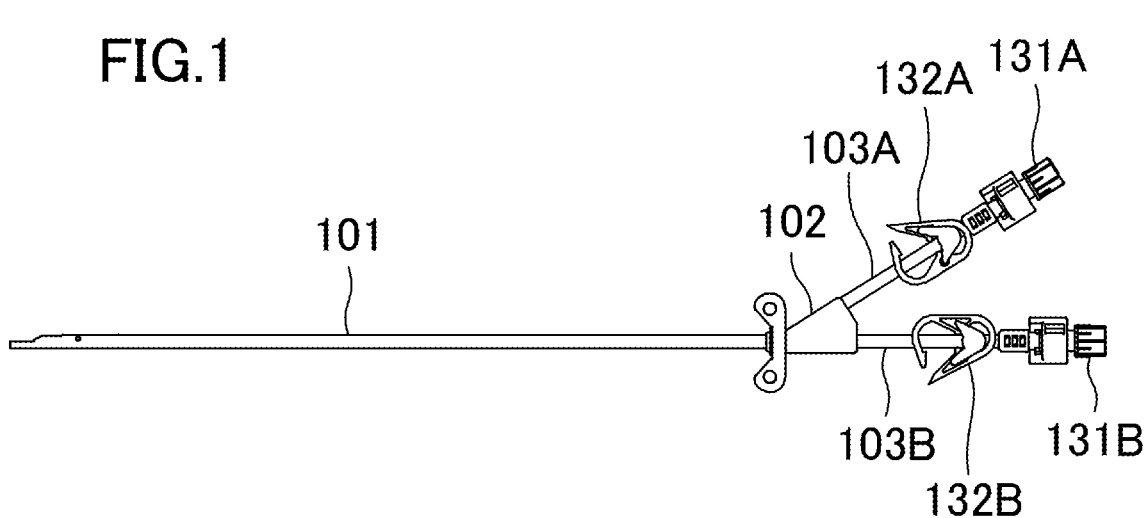
FIG. 1 is a side view of an entire multi-lumen catheter of one embodiment.
Figure 2:
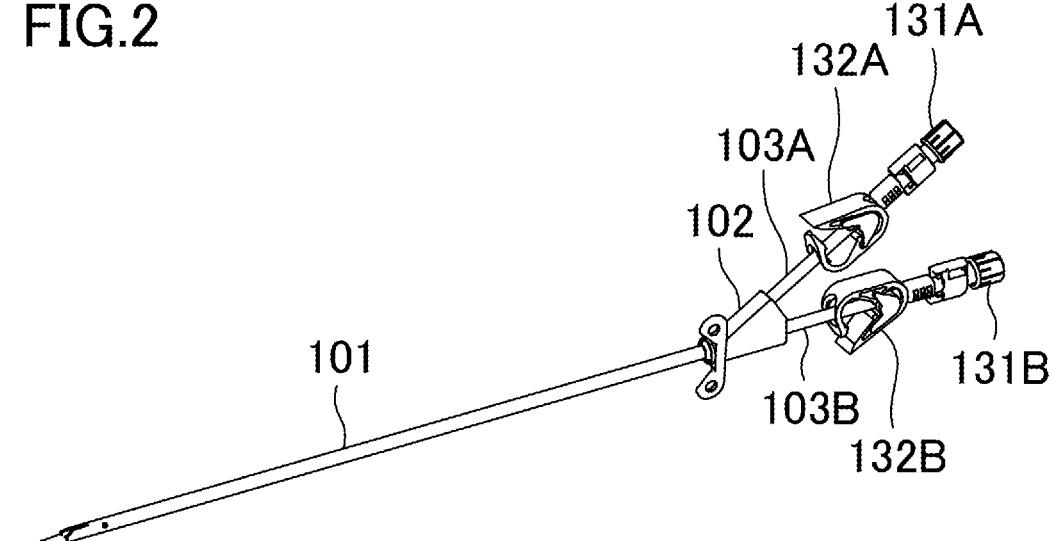
FIG. 2 is a perspective view of the entire multi-lumen catheter of the embodiment.
Figure 3:
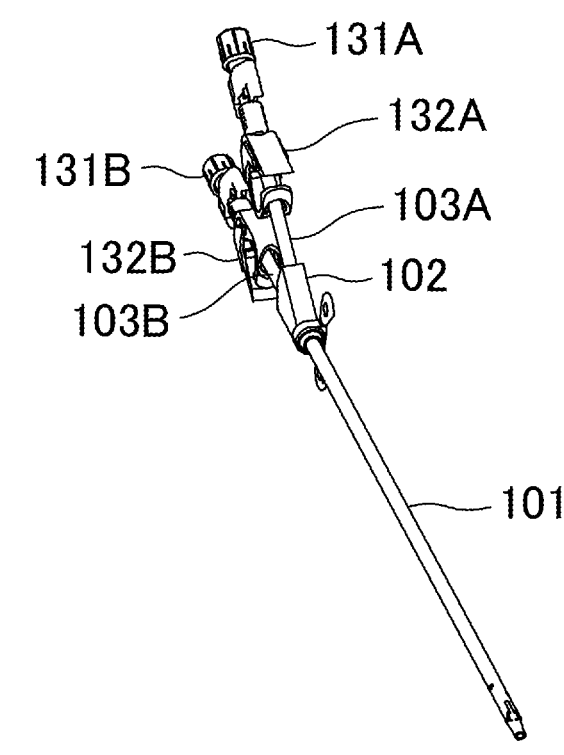
FIG. 3 is a perspective view of the entire multi-lumen catheter of the embodiment.
Figure 4:
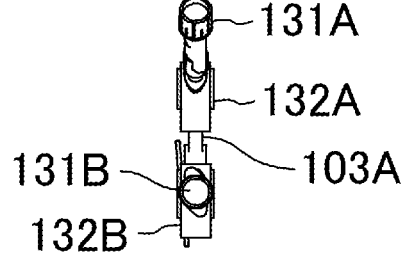
FIG. 4 is a view of the multi-lumen catheter of FIG. 1 viewed from its proximal end.
Figure 5:
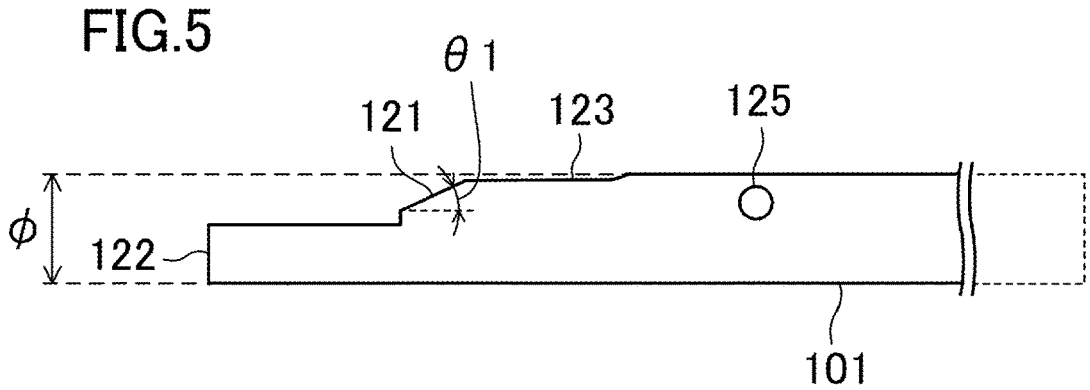
FIG. 5 is a right-side view of the multi-lumen catheter of the embodiment.
Figure 6:
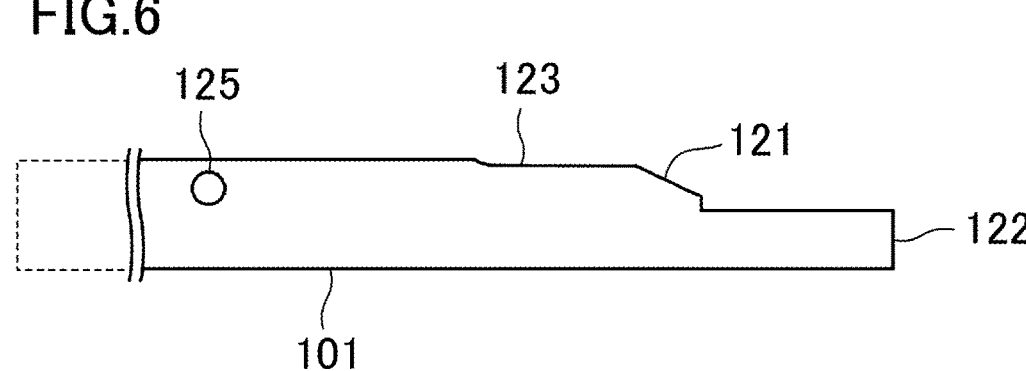
FIG. 6 is a left-side view of the multi-lumen catheter of the embodiment.

A multi-lumen catheter (which will be referred to just as "catheter" hereinafter) of the present disclosure is for use in hemodialysis, in which blood removed via a blood removal lumen of the catheter indwelled in a blood vessel is purified outside the patient's body and the blood thus purified is returned into the blood vessel via a blood return lumen of the catheter.

As illustrated in FIGS. 1 to 11, the catheter of this embodiment includes: a body (a catheter tube) 101 that is formed into a cylindrical shape and surrounded by an outer wall 113 extending from a proximal end to a distal end. The body 101 includes in its inner space a partition 114 extending in a longitudinal direction. The partition 114 divides the inner space of the body 101 into a first lumen 111 and a second lumen 112. The outer wall 113 includes a first outer wall portion 115 defining the first lumen 111 and a second outer wall portion 116 defining the second lumen 112. The first lumen 111 is defined by the first outer wall portion 115 and the partition 114, and the second lumen 112 is defined by the second outer wall portion 116 and the partition 114.

Although the use of the catheter of this embodiment is not limited in terms of which direction is the upward, downward, rightward, or leftward direction of the catheter, the following description assumes the following: With respect to the partition 114, the upper side is the side on which the first lumen 111 is located, and the lower side is the side on which the second lumen 112 is located. In addition, it is assumed that, with the first lumen 111 being on the upper side, the right side when the body 101 is viewed from the distal end side is referred to as a right-side surface, and the left side is referred to as a left-side surface.

In the hemodialysis using the catheter of this embodiment, to perform normal forward connection, the first lumen 111 serves as a blood removal lumen, and the second lumen 112 serves as a blood return lumen. In addition, in order to solve problems such as sticking to the blood vessel wall, it is also possible to perform reverse connection in which the first lumen 111 and the second lumen 112 are used with their functions exchanged. To perform such a reverse connection, the second lumen 112 serves as a blood removal lumen, and the first lumen 111 serves as a blood return lumen.

The first lumen 111 and the second lumen 112 are symmetrical with each other with respect to the partition 114. This configuration results in that the first lumen 111 and the second lumen 112 have an equal cross-sectional area, so that the amount of blood removed via the second lumen 112 can be easily ensured in the reverse connection as well. In addition, extrusion molding for manufacturing the body 101 is facilitated. Optionally, to ensure the amount of blood removed via the first lumen 111 in the forward connection, the partition 114 may be positioned in such a way that the first lumen 111 has a cross-sectional area greater than that of the second lumen 112.

The first lumen 111 and the second lumen 112 are semicircular in cross-section. This configuration ensures large cross-sectional areas of the first lumen 111 and the second lumen 112 by effectively utilizing the inner cavity of the body 101. With this configuration, the amount of blood removed via the first lumen 111 can be secured and the suction pressure can be lowered to make the sticking to the blood vessel wall difficult, during the forward connection. This configuration can also bring about the same effect for the second lumen 112 during the reverse connection.

The outer diameter q of the body 101 is not particularly limited, but may be preferably 2 mm or greater, or more preferably 2.5 mm or greater in light of ensuring the blood flow rate. Moreover, for the sake of the insertability into blood vessels, the outer diameter of the body 101 may be preferably 6 mm or smaller, or more preferably 5 mm or smaller.

The thickness of the outer wall 113 of the body 101 is not particularly limited, but may be preferably 0.1 mm or thicker, or more preferably 0.2 mm or thicker, in light of the strength of the catheter. Moreover, in light of the flexibility of the catheter, the thickness of the outer wall 113 of the body 101 may be preferably 0.8 mm or less, or more preferably 0.6 mm or less.

The catheter of this embodiment is of end hole-type with the first lumen 111 and the second lumen 112 each having a distal end opening, which opens toward a distal end of the body 101. The second lumen 112 has a second opening plane 122 at its distal end, and the first lumen 111 has a first opening plane 121 at its distal end, and the second opening plane 122 is positioned more distally than the first opening plane 121. In the catheter of this embodiment, the second opening plane 122 is positioned at the distal end of the body 101. With this configuration, the body 101 has such a distal end that has a smaller cross-sectional area than in a configuration in which the first opening plane 121 and the second opening plane 122 coincide with each other in the longitudinal direction, thereby improving the catheter in insertability. Moreover, with this configuration, recirculation, in which the blood returned via the second lumen 112 is sucked into the first lumen 111 immediately after the return, becomes more difficult to occur during the forward connection.

It is preferable that the first opening plane 121 is distanced from the second opening plane 122 as much as allowed, for the sake of the insertability of the catheter and of avoiding the recirculation during the forward connection. Specifically, a distance L1, which is a distance from the distal end of the body 101 (i.e., the second opening plane 122) to the first opening plane 121, may be preferably 3 mm or longer, or more preferably 7 mm or longer. In view of the length of the catheter, it is preferable that the distance from the distal end of the body 101 be not too long. Specifically, the distance L1, which is the distance from the distal end of the body 101 (i.e., the second opening plane 122) to the first opening plane 121, may be preferably 25 mm or shorter, or more preferably 15 mm or shorter.

The partition 114 extends from the proximal end to the distal end of the body 101. The width of the partition 114 is constant from the proximal end of the body 101 to the position of the first opening plane 121, and becomes gradually narrower from the position of the first opening plane 121 to the distal end of the body 101. The second outer wall portion 116 is configured such that the inner cavity of the second lumen 112 becomes gradually smaller toward the distal end of the body 101 in accordance with the change in the width of the partition 114. This configuration enables the catheter to be insertable with less resistance and less damaging to the blood vessel. Where to start the narrowing of the width of the partition 114 is not particularly limited. The width of the partition 114 may start to gradually narrow from any starting position, as long as the starting position is more distal than the first opening plane 121.

The first outer wall portion 115 is trimmed in such a way that the first outer wall portion 115 becomes farther from the partition 114 toward the proximal end, so that first opening plane 121 is declined with respect to the partition 114 toward the proximal end. This configuration enables the catheter to be insertable with less resistance and less damaging to the blood vessel, compared with a configuration in which the first opening plane 121 is orthogonal to the partition 114. Further, the inclination gives the first opening plane 121 a larger size (a larger opening plane area) than that in the case where the first opening plane 121 is orthogonal to the partition 114. With this configuration, the suction pressure can be reduced to make the sticking to the blood vessel wall difficult in the forward connection. Furthermore, this configuration enables to easily ensure the amount of blood removed via the first lumen 111.

The first opening plane 121 and the partition 114 forms an opening angle θ1 that may be preferably 60° or less, or more preferably 50° or less, for the sake of the insertability of the catheter. On the other hand, in light of preventing blood removal failure caused by the first opening plane 121 sticking to the blood vessel wall due to the suction pressure during the forward connection, the opening angle θ1 may be preferably 15° or more, or more preferably 25° or more.

The second opening plane 122 is orthogonal to the partition 114. This configuration can make it difficult for the sticking to the blood vessel wall to occur in the reverse connection.

The first outer wall portion 115 has a first lumen slit 123 obtained by notching a portion of the distal end of the first outer wall portion 115. The first lumen slit 123 has a predetermined width. With such a configuration, the flow of blood sucked into the first lumen 111 is dispersed also into the first lumen slit 123 during forward connection. This reduces the suction pressure, thereby making it difficult for the sticking to the blood vessel wall to occur. With this configuration, even if the first opening plane 121 is clogged due to thrombus or the like, the first lumen 111 can be kept open.

The first lumen slit 123 is provided in a circumferential middle portion of the first outer wall portion 115. This configuration allows the catheter to be indwelled in the blood vessel without lowering the rigidity of the first outer wall portion 115. In addition, this configuration enables to prevent clogging or narrowing of the first opening plane 121 that would be caused by pressing from the blood vessel wall or the like.

The first lumen slit 123 may be formed by notching from the distal end of the first outer wall portion 115 and heating the notch. In this way, the first lumen slit 123 can be easily formed without requiring a complicated process. In addition, according to this configuration, burrs are less likely to be generated in the formation of the first lumen slit 123, and thus this configuration is excellent in safety.

The length L2 of the first lumen slit 123 is not particularly limited, but may be preferably not shorter than 2 mm but not longer than 15 mm, or more preferably not shorter than 5 mm but not longer than 10 mm, for the sake of reducing the sticking to the blood vessel wall.

The width of the first lumen slit 123 is not particularly limited, but may be preferably not shorter than 0.1 mm but not longer than 2.5 mm. Moreover, the width of the first lumen slit 123 may be preferably in a range of 2.5% to 63% of an outer diameter φ of the catheter, for the sake of ensuring the rigidity of the first outer wall portion 115. The width of first lumen slit 123 is constant in the longitudinal direction in this embodiment, but is not limited thereto and may vary along the longitudinal direction. For example, the width of the first lumen slit 123 may be gradually widened from the distal end to the proximal end of the first lumen slit 123.

The distal end portion of the first outer wall portion 115 has (a) first lumen side pore(s) 125 allowing the first lumen 111 to communicate with the outside of the first lumen 111. With such a configuration, the flow of blood sucked into the first lumen 111 is further dispersed during the forward connection, thereby further making it difficult for the sticking to the blood vessel wall to occur. Moreover, this configuration enables to easily ensure the amount of blood removed via the first lumen 111. Furthermore, this configuration enables to keep the first lumen 111 open even if the first opening plane 121 and/or the first lumen slit 123 is/are clogged due to thrombus or the like.

It is preferable to provide a plurality of the first lumen side pores 125 at intervals in the longitudinal direction, in order to attain a greater effect of dispersing the suction pressure. The catheter of this embodiment is illustrated as having two first lumen side pores 125, but the number of the first lumen side pores 125 is not limited thereto and may be three or more.

For the sake of reducing the sticking to the blood vessel wall, it is preferable that the first lumen side pore(s) 125 be displaced from the first lumen slit 123 as much as possible, and it is more preferable that the first lumen side pore(s) 125 be positioned more proximally than the first lumen slit 123. Moreover, the sticking to the blood vessel wall can be further reduced by making the positions of the plurality of the first lumen side pores 125 displaced, that is, staggered from each other in both the longitudinal direction and the width direction of the first lumen 111.

In the configuration in which the positions of the first lumen side pores 125 are staggered, it is preferable that positions of first lumen side pores 125 adjacent to each other be displaced as much as possible. For example, such two first lumen side pores 125 adjacent to each other may be preferably positioned such that lines connecting either one of adjacent two first lumen side pores 125 with the center of a circle formed by the outer wall 113 form an angle in a range of 110° to 160°. It is preferable that the first lumen side pores 125 be on opposite sides across the first lumen slit 123.

It is preferable that the first lumen side pores 125 be positioned at equal intervals in the longitudinal direction. For example, such two first lumen side pores 125 adjacent to each other may be preferably arranged at such a longitudinal interval that the length of a straight line connecting the centers of the first lumen side pores 125 assumingly aligned straightly in the longitudinal direction be in a range of 2 mm to 5 mm. The first lumen side pores 125 may be arranged at inconstant intervals in the longitudinal direction. The positions of the first lumen side pores 125 are not limited to the staggering arrangement, but may be aligned straightly in the longitudinal direction.

The diameter(s) of the first lumen side pore(s) 125 is/are not particularly limited, but may be preferably not smaller than 0.5 mm, but not greater than 2.0 mm. A part of the plurality of the first lumen side pores 125 may differ from the others in their diameters. Moreover, the first lumen side pore(s) 125 may be provided as needed, and the catheter may be configured without the first lumen side pore(s) 125.

The body 101 includes a flexible portion 141. The flexible portion 141 has a lower hardness than the other portion 142 of the body 101 other than the flexible portion 141. The flexible portion 141 includes the distal end portion of the first outer wall portion 115, in which the first lumen slit 123 is formed.

Figure 7:
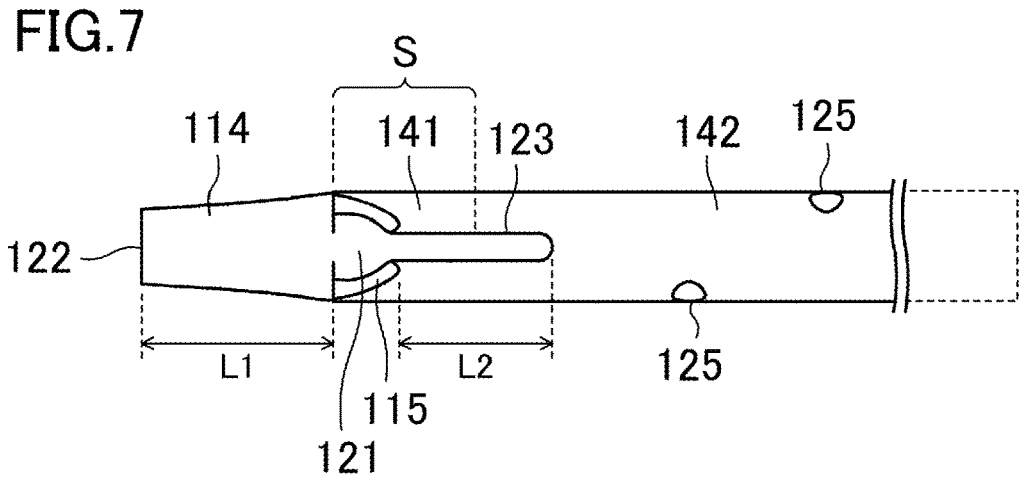
FIG. 7 is a top view of the multi-lumen catheter of the embodiment.
Figure 8:
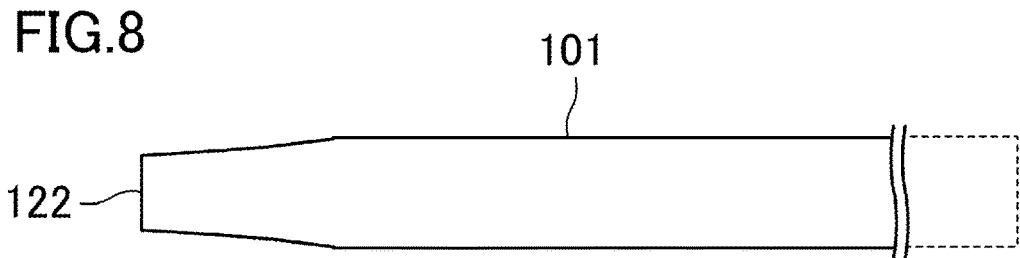
FIG. 8 is a bottom view of the multi-lumen catheter of the embodiment.
Figure 9:
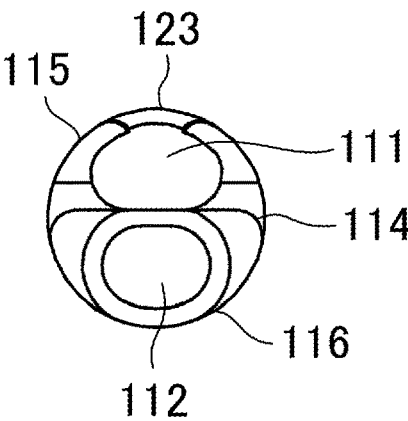
FIG. 9 is a view of the multi-lumen catheter of FIG. 5 viewed from its distal end.
Figure 10:
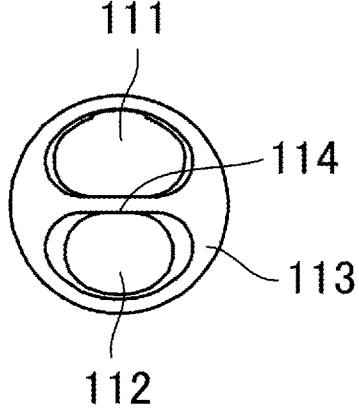
FIG. 10 is a view of the multi-lumen catheter of FIG. 5 viewed from its proximal end.
Figure 11:
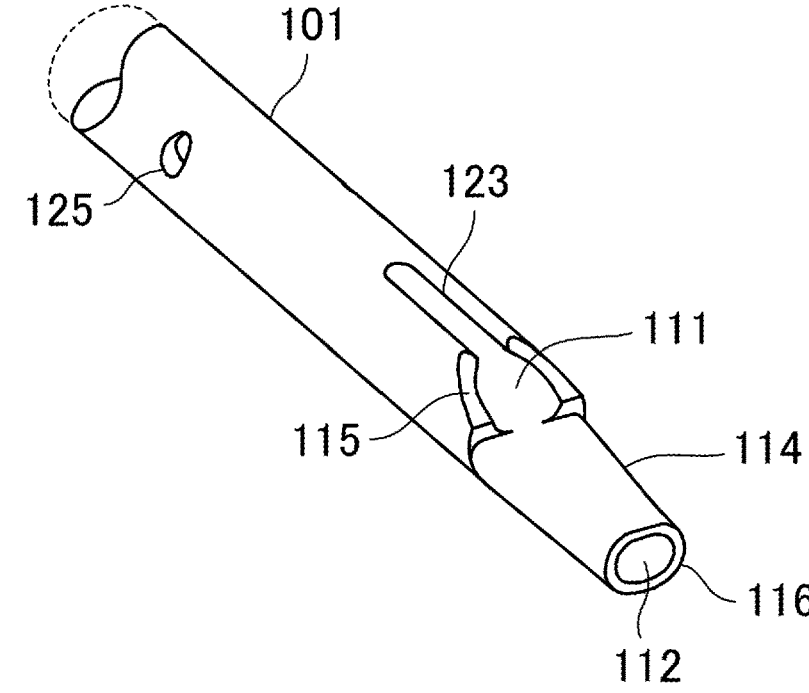
FIG. 11 is a perspective view of the multi-lumen catheter of the embodiment.

As illustrated in FIG. 7, the distal end portion, included in the flexible portion 141, of the first outer wall portion 115 is a portion S that extends from the distal end to a position corresponding to at least the middle of the length L2 of the first lumen slit 123 within the portion that includes the first lumen slit 123 of the first outer wall portion 115. Thus, the flexible portion 141 includes the portion S, which is at least a distal half of the portion, where the first lumen slit 123 is provided, of the first outer wall portion 115. Note that the flexible portion 141 may cover further extended area, and, for example, may be configured to include the entire portion where the first lumen slit 123 is provided.

These configurations bring about the following effect: At the catheter insertion, the catheter is deformed in such a way that the distal end portion of the first outer wall portion 115 bends into the inner cavity of the first lumen 111 from both sides of the first lumen slit 123. This allows the catheter to have the following excellent insertability: At the insertion, the cross-sectional area of the body 101 at the first opening plane 121 becomes smaller, so that the first opening plane 121 will not be a cause of significant insertion resistance. In addition, this allows for reduction in the burden on the patient and the operator. The distal end portion of the first outer wall portion 115 returns to its original shape when the catheter is indwelled in the blood vessel. This allows for an excellent insertability of the catheter without affecting the function of the first lumen 111.

The flexible portion 141 may preferably include such a part of the portion of the first outer wall portion 115 where the first lumen slit 123 is provided, extending from the position of the proximal end of the first lumen slit 123 to the distal end of the portion. With this configuration, the first outer wall portion 115 becomes more easily deformable from both sides of the first lumen slit 123 in such a way that the first outer wall portion 115 bends into the inner cavity of the first lumen 111 from where the proximal end of the first lumen slit 123 is located. This allows the catheter to have such a more excellent insertability, because, at the insertion, the cross-sectional area of the body 101 at the first opening plane 121 becomes further smaller, so that the insertion resistance changes more gradually.

Moreover, the flexible portion 141 may preferably include a portion that ranges from the position of the proximal end of the first lumen slit 123 to the distal end of the body 101 (i.e., the second opening plane 122). This configuration allows the catheter to have an excellent insertability and makes the catheter less damaging to the blood vessel in passing through the blood vessel.

In the configuration in which the flexible portion 141 includes a portion that ranges from the position of the proximal end of the first lumen slit 123 to the distal end of the body 101 (i.e., the second opening plane 122), the longitudinal range of the flexible portion 141 from the distal end of the body 101 may be preferably 5 mm or longer, or more preferably 10 mm or longer, for the sake of the insertability of the catheter. On the other hand, for the sake of operability of the catheter, the longitudinal range of the flexible portion 141 from the distal end of the body 101 may be preferably 50 mm or shorter, or more preferably 40 mm or shorter.

The flexible portion 141 may be formed of a material such as polyurethane, polyvinyl chloride, silicone, an ethylene-vinyl acetate copolymer, or a polyamide. Among them, the flexible portion 141 may be preferably formed of polyurethane.

In addition, the other portion 142 than the flexible portion 141 in the body 101 is required to be stable in shape in the blood vessel and to have hardness to an extent that does not damage the blood vessel. In view of this, the other portion 142 than the flexible portion 141 may be formed of a material such as polyurethane, polyvinyl chloride, silicone, polyethylene, polypropylene, an ethylene-vinyl acetate copolymer, or a polyamide. Moreover, among them, the other portion 142 than the flexible portion 141 may be preferably formed of polyurethane, because polyurethane has such a hardness that does not impair the insertability of the catheter and polyurethane is hard at room temperatures, but becomes softer at internal body temperatures. The flexible portion 141 and the other portion 142 than the flexible portion 141 may be preferably formed of the same material for the sake of easy welding, but may be formed of different materials.

In a case where the other portion 142 than the flexible portion 141 is made of a material whose hardness decreases significantly as temperature rises, the flexible portion 141 and the other portion 142 other than the flexible portion 141 have a predetermined difference in hardness at room temperatures before catheter insertion. On the other hand, at the catheter insertion in a blood vessel and warmed up at an internal body temperature, the hardness of the other portion than the flexible portion 141 decreases significantly, so that the difference in hardness between the flexible portion 141 and the other portion 142 than the flexible portion 141 becomes smaller than before the insertion. This configuration prevents the catheter from bending at a boundary between the flexible portion 141 and the other portion 142 than the flexible portion 141 inside the blood vessel, thereby making the catheter less damaging to the blood vessel, even though the insertability of the catheter is still maintained.

The distal end of the body 101 may have a color different from the color of the other portion of the body 101. This facilitates the operator to recognize the position of the distal end of the body 101, thereby improving the operability of the catheter. At least a portion of the body 101 may be formed of a material containing a contrast agent such as barium sulfate, bismuth tungstate, or bismuth oxide, so as to facilitate finding out where the catheter is inserted.

The length of the body 101 is not particularly limited, but may be preferably 10 cm or longer, or more preferably 13 cm or longer, but preferably 40 cm or shorter, or more preferably 30 cm or shorter, as an indwelling portion of the catheter.

The body 101 is provided with branch pipes 103A and 103B extending from the proximal end of the body 101 via a branch portion 102. A distal end of the branch pipe 103A is connected to the first lumen 111. Moreover, the distal end of the branch pipe 103B is connected to the second lumen 112. Each of the proximal ends of the branch pipes 103A and 103B is provided with a connector (not shown) connected thereto. The connectors, which are covered respectively with protection caps 131A and 131B in the illustrations in FIGS. 1 to 4, allow the body 101 to be connected to a blood circuit and the like via the connectors.

The branch pipe 103A is provided with a clamp 132A attached thereto, whereas the branch pipe 103B is provided with a clamp 132B attached thereto. By providing the branch pipes 103A and 103B respectively with the clamps 132A and 132B, the branch pipes 103A to 103B becomes closable for performing a treatment such as heparin lock.

The catheter of this embodiment can be modified in various ways. In the following variations, only portions different from this embodiment will be described. The description of the configuration common to the present embodiment will be omitted as appropriate. In addition, like portions are denoted with like reference numerals as in this embodiment.

Figure 12:
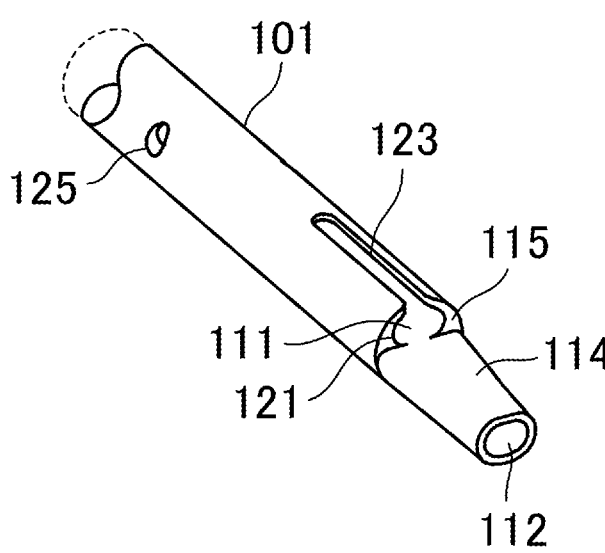
FIG. 12 is a perspective view of a multi-lumen catheter of a first variation.

According to a first variation, as illustrated in FIG. 12, the first opening plane 121 may be orthogonal to the partition 114. This configuration enables to make it difficult for the sticking to the blood vessel wall to occur in the forward connection. In the first variation, at the catheter insertion, the first outer wall portion 115 is deformed from the both sides of the first lumen slit 123 in such a way that the distal end portion of the first outer wall portion 115 goes into the inner cavity of the first lumen 111. This allows for preventing the first opening plane 121 orthogonal to the partition 114 from becoming an insertion resistance.

Figure 13:
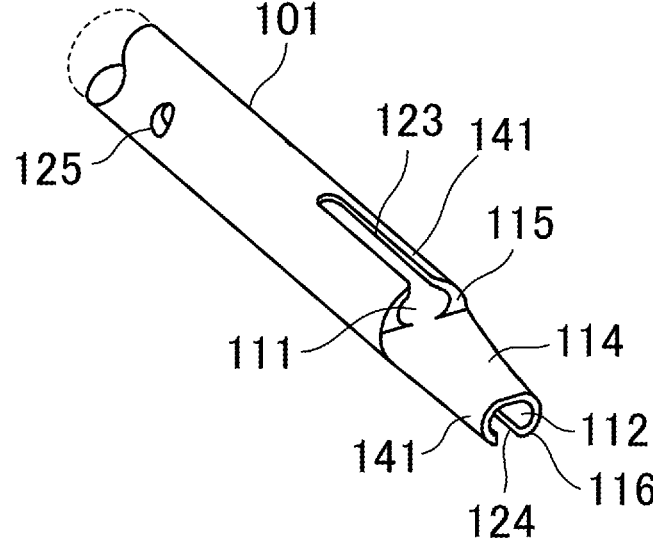
FIG. 13 is a perspective view of a multi-lumen catheter of a second variation.
Figure 14:
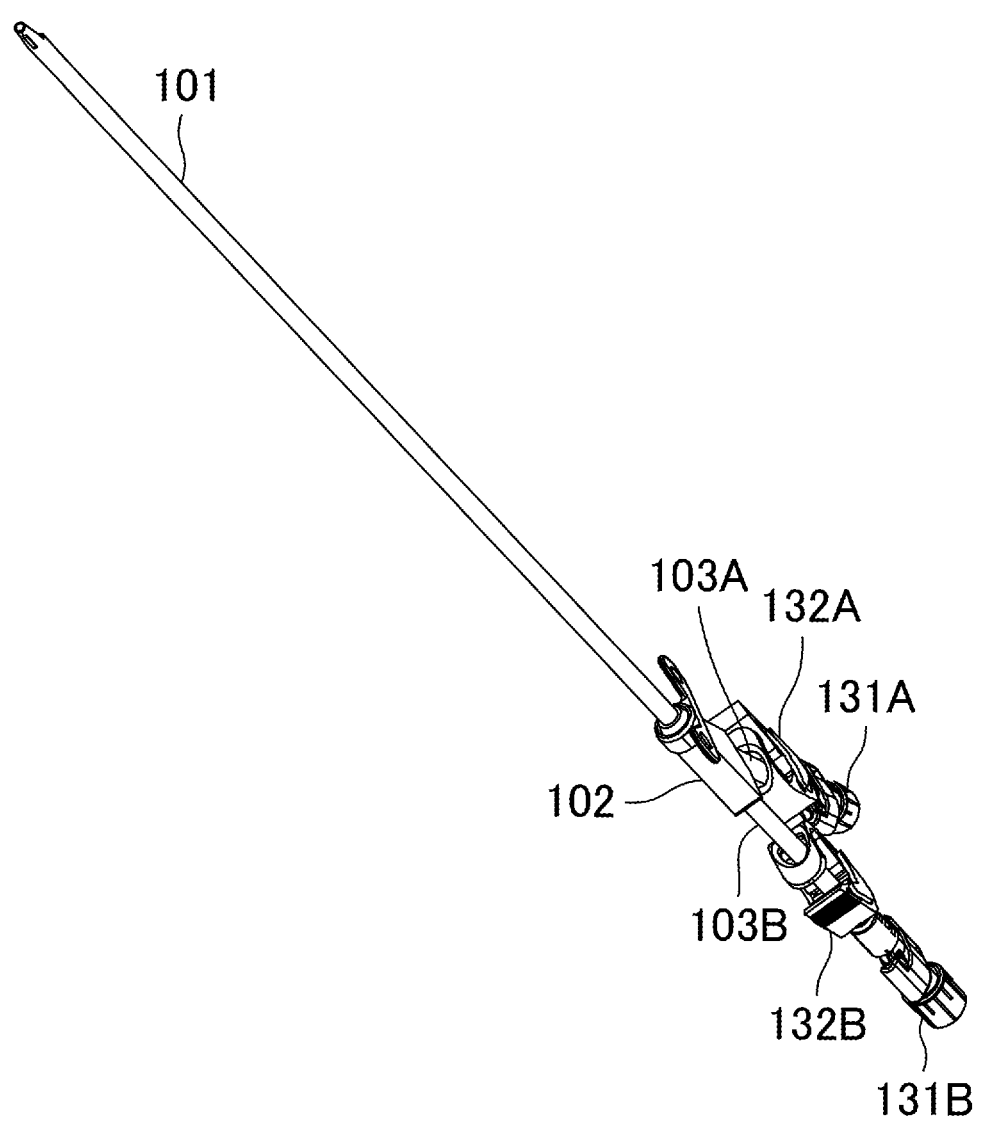
FIG. 14 is a perspective view of an entire multi-lumen catheter of a fourth variation.
Figure 19:
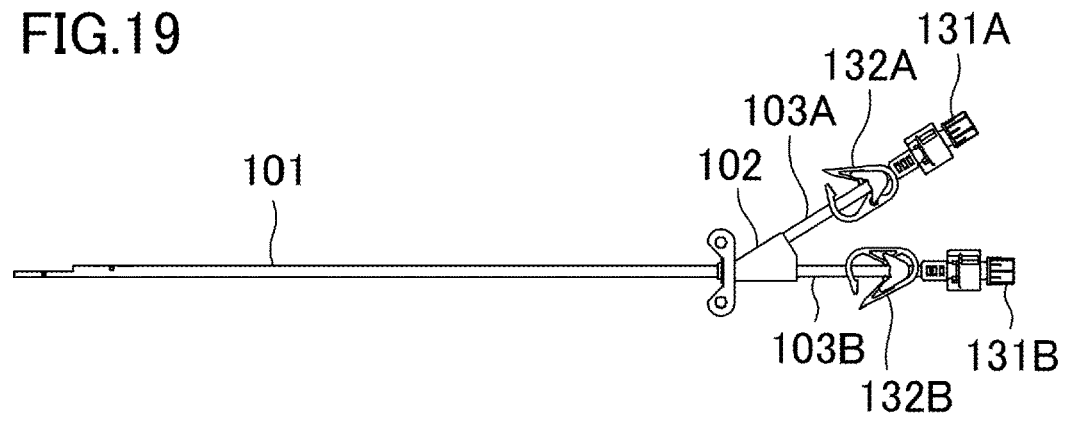
FIG. 19 is a side view of an entire multi-lumen catheter of a fifth variation.
Figure 20:
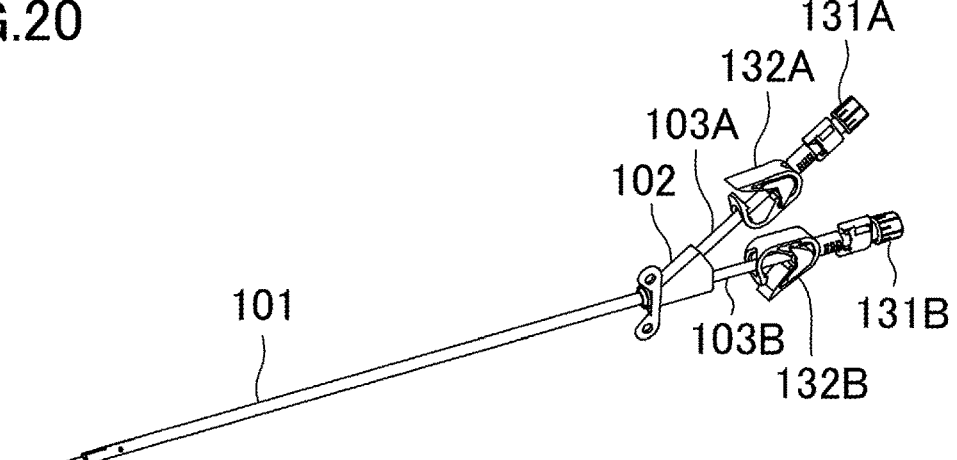
FIG. 20 is a perspective view of an entire multi-lumen catheter of the fifth variation.
Figure 21:
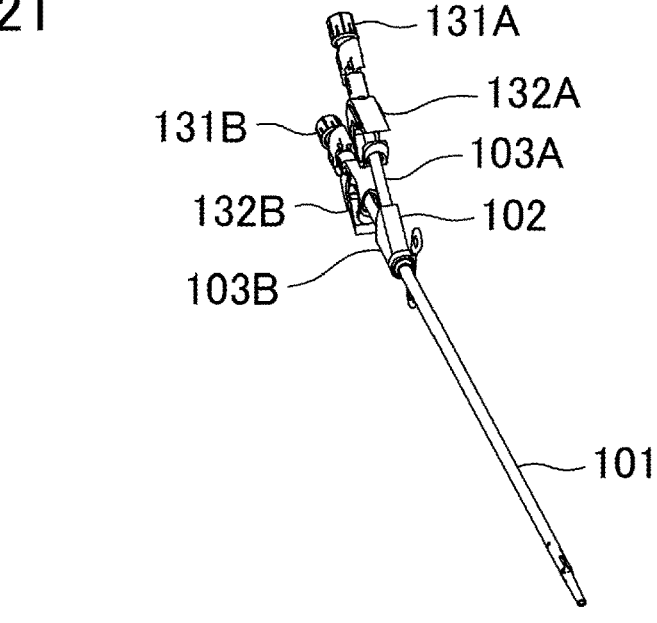
FIG. 21 is a perspective view of an entire multi-lumen catheter of the fifth variation.
Figure 22:
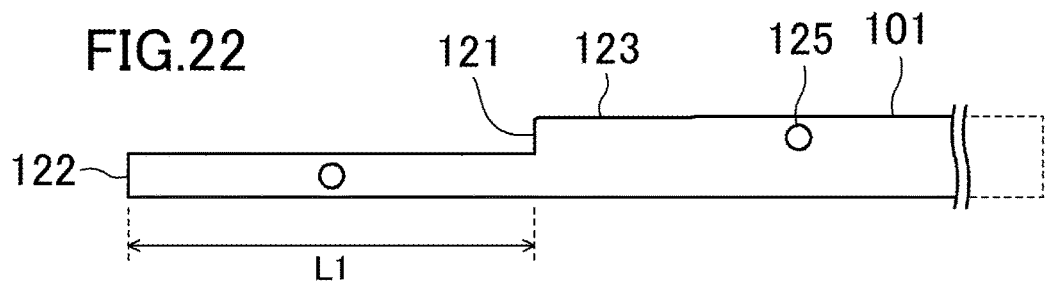
FIG. 22 is a right-side view of the multi-lumen catheter of the fifth variation.
Figure 23:
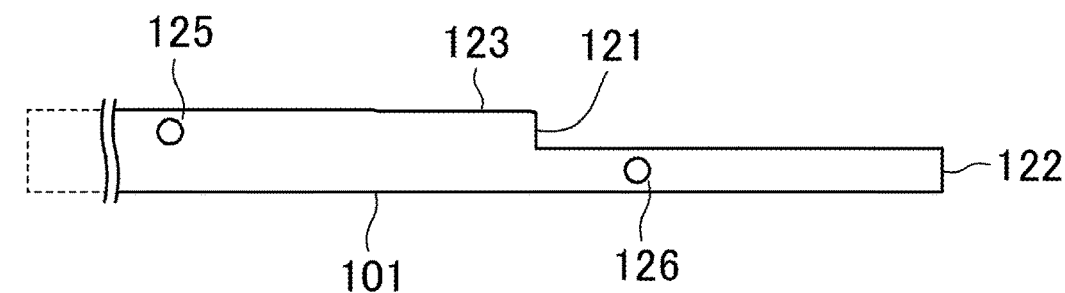
FIG. 23 is a left-side view of the multi-lumen catheter of the fifth variation.
Figure 24:
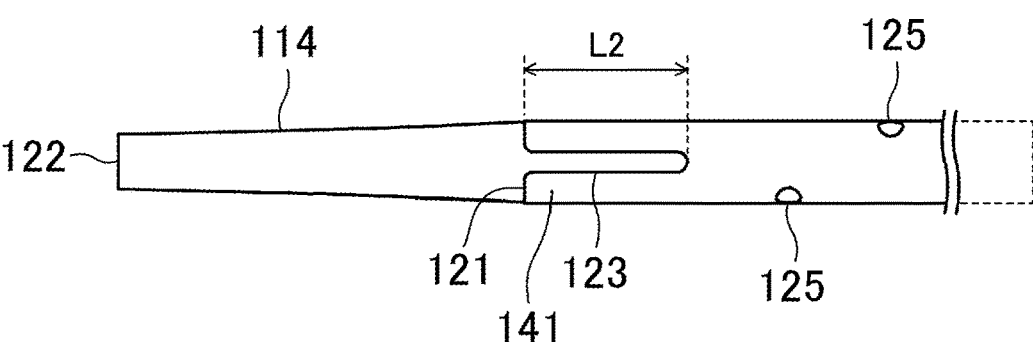
FIG. 24 is a top view of the multi-lumen catheter of the fifth variation.
Figure 25:
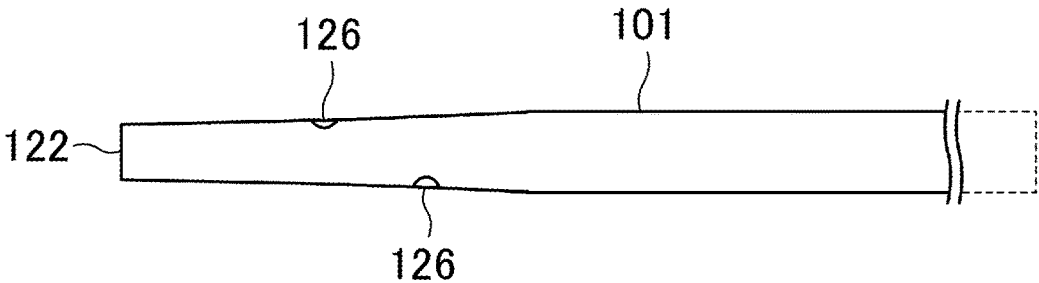
FIG. 25 is a bottom view of the multi-lumen catheter of the fifth variation.
Figure 26:
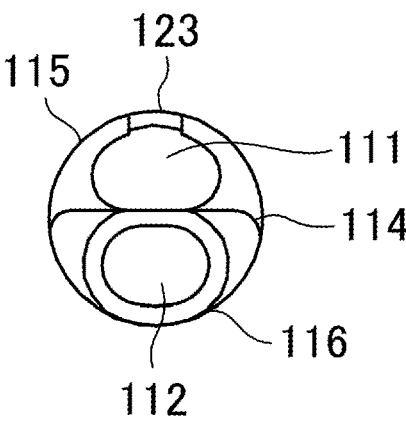
FIG. 26 is a view of the multi-lumen catheter of FIG. 22 viewed from its distal end.
Figure 27:
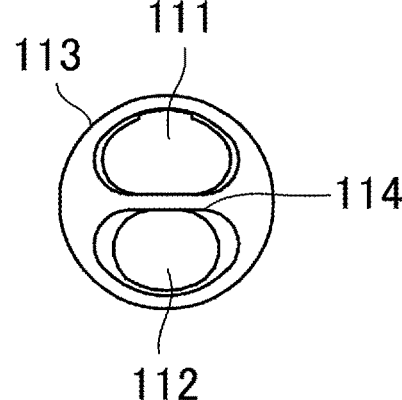
FIG. 27 is a view of the multi-lumen catheter of FIG. 22 viewed from its proximal end.
Figure 28:
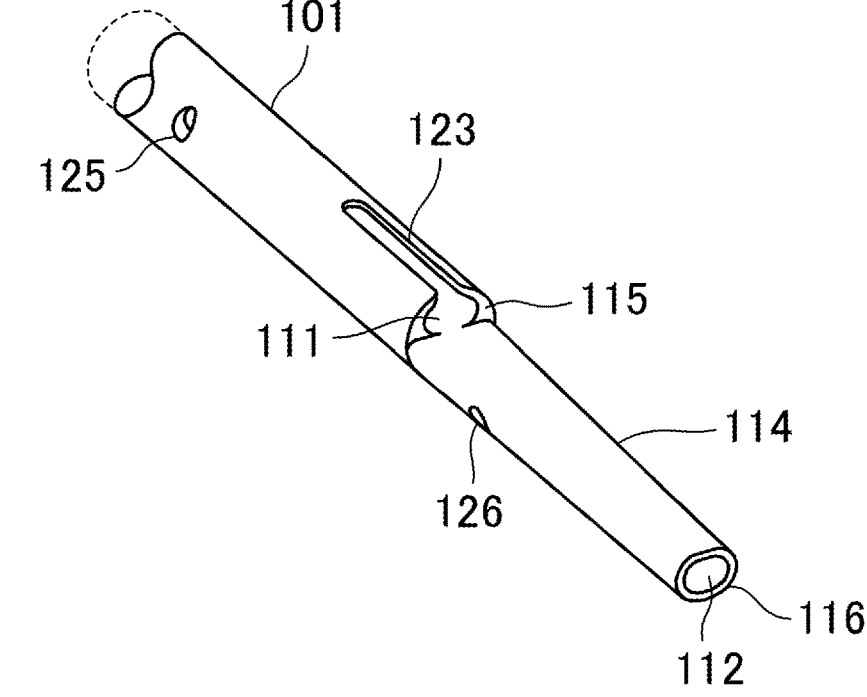
FIG. 28 is a perspective view of a multi-lumen catheter of the fifth variation.

According to a second variation, as illustrated in FIG. 13, the distal end of the second outer wall portion 116 may have a second lumen slit 124. With such a configuration, the flow of blood sucked into the second lumen 112 is dispersed, reducing the suction pressure during reverse connection, thereby making it difficult for the sticking to the blood vessel wall to occur. This configuration enables to make it difficult for recirculation to occur in the reverse connection.

The second lumen slit 124 may be provided preferably in a circumferential middle portion of the second outer wall portion 116, for the sake of preventing rigidity reduction of the second outer wall portion 116. The length of the second lumen slit 124 is not particularly limited, but may be preferably 2 mm or longer or 15 mm or shorter for the sake of reducing the sticking to the blood vessel wall. Moreover, the width of the second lumen slit 124 is not particularly limited, but may be preferably 0.1 mm or wider, but 2.5 mm or narrower, and preferably in a range of 2.5% to 63% of the outer diameter φ of the catheter, in light of ensuring the rigidity of the second outer wall portion 116.

In the second variation, the flexible portion 141 includes, in addition to the distal end portion of the first outer wall portion 115, that distal end portion of the second outer wall portion 116, in which the second lumen slit 124 is provided. Here, the distal end portion of the second outer wall portion 116 included in the flexible portion 141 is a part of the portion in which the second lumen slit 124 of the second outer wall portion 116 is provided, the part at least ranging from the half of the length of the second lumen slit 124 to the distal end. Therefore, it is sufficient that the flexible portion 141 provided in the second outer wall portion 116 includes the distal half of the portion in which the second lumen slit 124 of the second outer wall portion 116 is provided, and the flexible portion 141 may include the entire portion in which the second lumen slit 124 is provided.

This configuration brings about the following effect: At the catheter insertion, the catheter is deformed in such a way that the distal end portion of the second outer wall portion 116 bends into the inner cavity of the second lumen 112 from both sides of the second lumen slit 124. With this configuration, at the insertion, the cross-sectional area of the body 101 at the second opening plane 122 becomes smaller, thereby providing the catheter with an excellent insertability. The distal end portion of the second outer wall portion 116 returns to its original shape when the catheter is indwelled in the blood vessel. This allows for an excellent insertability of the catheter without affecting the function of the second lumen 112.

The flexible portion 141 provided on the first outer wall portion 115 and the flexible portion 141 provided on the second outer wall portion 116 may be separate portions or a continuous portion. Specifically, the configuration where the flexible portions 141 are separate portions may be, for example, the following case: The flexible portions 141 are provided respectively at the portion including the distal end portion of the first outer wall portion 115 and at the portion including the distal end portion of the second outer wall portion 116. Moreover, the configuration where the flexible portions 141 are a continuous portion may be, for example, the following case: The flexible portion 141 includes a portion that ranges from the position in the body 101 at which the proximal end of the first lumen slit 123 is located, to the distal end of the body 101 (second opening plane 122).

According to a third modified example (not shown), from the viewpoint of preventing recirculation in the reverse connection, the second variation may be further modified such that the first opening plane 121 and the second opening plane 122 are provided together at the distal end of the body 101 so as to be coincided longitudinally, and the partition 114 is extended more distally than the positions of the first opening plane 121 and the second opening plane 122. In this configuration, the recirculation in reverse connection is more difficult to occur than in the configuration in which the second opening plane 122 is more distal than the first opening plane 121.

Moreover, in the third variation, the second outer wall portion 116 has a second lumen slit 124 and the flexible portion 141 includes, in addition to the distal end portion of the first outer wall portion 115, that distal end portion of the second outer wall portion 116 on the both sides of the second lumen slit 124. This configuration brings about the following effect: At the catheter insertion, the catheter is deformed in such a way that the first outer wall portion 115 and the second outer wall portion 116 bend into the inner cavities of the first lumen 111 and the second lumen 112. Thus, even in the configuration in which the first opening plane 121 and the second opening plane 122 are coincided longitudinally, the cross-sectional area at the distal end of the body 101 can become smaller, thereby obtaining an excellent insertability of the catheter.

The third variation is especially preferable in the case where the catheter is inserted with the aid of an introducer sheath. When inserting the catheter into an inner cavity of the introducer sheath, the first outer wall portion 115 and the second outer wall portion 116 are deformed, so that the catheter can pass through the check valve easily. Furthermore, the recirculation in reverse connection can be reduced by the partition 114 extended more distally beyond the positions of the first opening plane 121 and the second opening plane 122.

According to a fourth variation, as illustrated in FIGS. 14 to 18, the distal end portion of the second outer wall portion 116 may have a plurality of the second lumen side pores 126 communicating the second lumen 112 with the outside, the plurality of the second lumen 112 including a second lumen side pore 126 being elliptical in shape and long in the longitudinal direction. This can reduce the suction pressure in the reverse connection, thereby making it difficult for the sticking to the blood vessel wall to occur. Moreover, this configuration enables to easily ensure the amount of blood removed via the second lumen 112. Furthermore, this configuration can keep the second lumen 112 open by the plurality of second lumen side pores 126 even if the second opening plane 122 is clogged due to thrombus or the like.

The size of the second lumen side pore 126 being elliptical in shape is not particularly limited, but may be preferably as large (long and wide) as the second lumen slit 124, for the sake of reducing the sticking to the blood vessel wall.

The second lumen side pore 126 being elliptical in shape brings about a more advantageous effect than the second lumen slit 124, for example, when inserting the catheter by the Seldinger technique. Specifically, in performing the Seldinger technique, in the case of the configuration provided with the second lumen slit 124, insertion of the catheter with the aid of a stylet for filing a gap between the blood return lumen and a guide wire would cause a distal end of the stylet to stick out of the second lumen 112 via the second lumen slit 124, thereby damaging the blood vessel with the stylet or adversely affecting the operability of the catheter. On the other hand, the elliptical shape of the second lumen side pore 126 is closed loop-shaped, such sticking-out of the stylet will not occur and an excellent operability can be obtained.

Moreover, the distal end portion of the second outer wall portion 116 has a plurality of second lumen side pores 126 being circular in shape. The positions of the plurality of the second lumen side pores 126 being circular in shape may be preferably staggered from each other as in the case of the first lumen side pores 125, for the sake of reducing the sticking to the blood vessel wall in the reverse connection. While the fourth variation is illustrated as including two second lumen side pores 126 being circular in shape, three or more second lumen side pores 126 may be provided and the plurality of the second lumen side pores 126 may be aligned straightly in the longitudinal direction.

It is preferable that the second lumen side pore(s) 126 be positioned more distally than the position of the proximal end of the first lumen slit 123, for the sake of reducing the recirculation.

In the fourth variation, the flexible portion 141 includes the distal end portion of the first outer wall portion 115, the distal end portion having the first lumen slit 123. For facilitating the formation of the plurality of second lumen side pores 126, it is preferable that the flexible portion 141 do not include the distal end portion of the second outer wall portion 116. This configuration prevents breakage of the peripheries of the second lumen side pores 126, thereby ensuring the strength of the peripheries of the second lumen side pores 126, during hemodialysis.

The flexible portion 141 may include the distal end portion of the second outer wall portion 116, for example, in such a way that the flexible portion 141 includes a portion that ranges from the position of the proximal end of the first lumen slit 123 to the distal end of the body 101. This configuration brings about the following effect: At the catheter insertion, the distal end portion of the second outer wall portion 116 can be easily deformed, so that the second lumen side pore(s) 126 is/are narrowed or closed to reduce the cross-sectional area of the second lumen 112, thereby improving the insertability of the catheter. In the configuration in which the flexible portion 141 includes the distal end portion of the second outer wall portion 116, the distal end portion of the second outer wall portion 116 may be thick, for the sake of preventing breakage of the peripheries of the second lumen side pore(s) 126.

While the fourth variation is illustrated such that the plurality of the second lumen side pores 126 includes an elliptical one, all the plurality of the second lumen side pores 126 may be circular in shape. Optionally, the plurality of second lumen side pores 126 may be all elliptical in shape with no second lumen side pore 126 circular in shape, and the number of the second lumen side pores 126 is not particularly limited and may be one or more.

In the fourth variation, the cross sections of the distal end and the proximal end of the body 101 are similar to those of the catheter according to the present embodiment.

According to a fifth variation, as illustrated in FIGS. 19 to 28, the distance L1 from the first opening plane 121 to the distal end of the body 101 may be long, so that a plurality of the second lumen side pores 126 is provided in the distal end portion of the second outer wall portion 116. The long distance L1 allows the distal end portion of the second outer wall portion 116 to have a greater area, thereby ensuring places for positioning the plurality of second lumen side pores 126. In addition, this configuration can improve the insertability of the catheter by suppressing a rapid change in insertion resistance. The plurality of second lumen side pores 126 is provided, so that the flow of blood sucked into the second lumen 112 can be dispersed during the reverse connection, thereby making it difficult for the sticking to the blood vessel wall to occur.

The plurality of second lumen side pores 126 may be preferably provided at intervals in the longitudinal direction for the sake of dispersing the suction pressure during the reverse connection. It is preferable that the plurality of second lumen side pores 126 be positioned more distally than the first opening plane 121, for the sake of reducing the recirculation. While the fifth variation is illustrated as including two second lumen side pores 126, the number of the second lumen side pores 126 is not particularly limited, and three or more second lumen side pores 126 may be provided.

In view of reducing the sticking to the blood vessel wall, the positions of the plurality of second lumen side pores 126 may be preferably staggered. In this case, it is preferable that the positions of adjacent second lumen side pores 126 be displaced from each other as much as possible. The positions of the second lumen side pores 126 are not limited to the staggering arrangement, but may be aligned straightly in the longitudinal direction. Moreover, the fifth variation may further include a second lumen side pore 126 being elliptical in shape.

In the fifth variation, the flexible portion 141 may include the distal end portion of the first outer wall portion 115 where the first lumen slit 123 is provided, while the flexible portion 141 does not include the distal end portion of the second outer wall portion 116 for the sake of including the plurality of the second lumen side pores 126. This configuration prevents breakage of the peripheries of the second lumen side pores 126, thereby ensuring the strength of the peripheries of the second lumen side pores 126, during hemodialysis. Note that the flexible portion 141 may include the distal end portion of the second outer wall portion 116. In this case, the distal end portion of the second outer wall portion 116 may be thick, for the sake of preventing breakage of the peripheries of the second lumen side pore(s) 126.

The fifth variation is such that the distance L1 from the distal end of the body 101 (the second opening plane 122) to the first opening plane 121 may be preferably 30 mm or shorter, or more preferably 25 mm or shorter, for the sake of securing the place of providing the plurality of second lumen side pores 126, while improving the insertability of the catheter.

Figure 29:
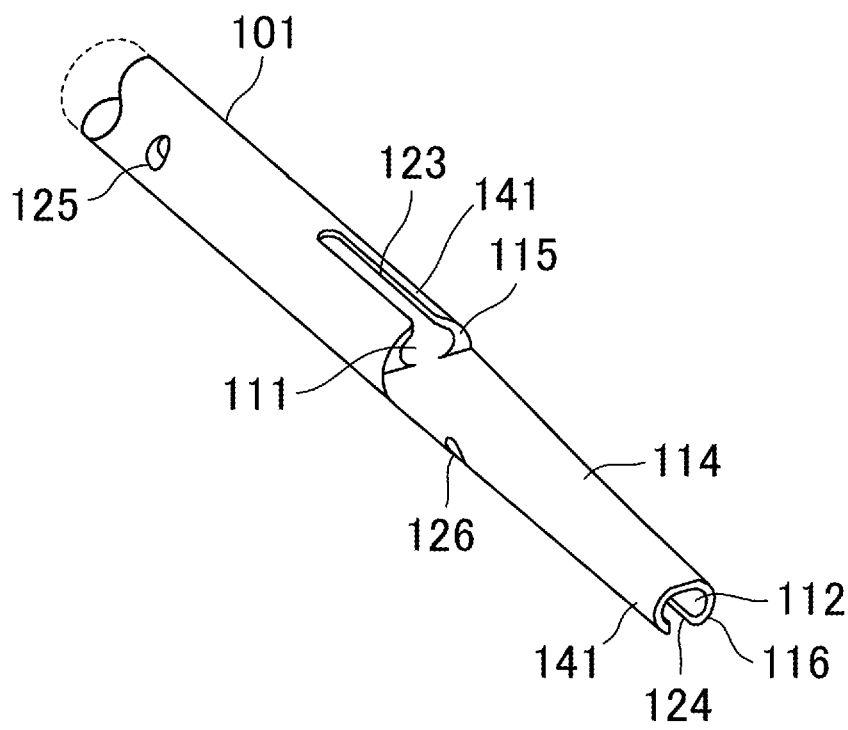
FIG. 29 is a perspective view of a multi-lumen catheter of a sixth variation.

According to a sixth variation, as illustrated in FIG. 29, the distal end of the second outer wall portion 116 may have a second lumen slit 124 and the second lumen side pore 126. With this configuration, the second lumen slit 124 can prevent the second outer wall portion 116 from sticking to the blood vessel wall in the longitudinal direction while the second lumen side pore 126 can prevent the second outer wall portion 116 from sticking to the blood vessel wall in the circumferential direction.

Moreover, as in the second variation and the third variation, the sixth variation is configured such that the flexible portion 141 includes, in addition to the distal end portion of the first outer wall portion 115, the distal end portion of the second outer wall portion 116 where the second lumen slit 124 is provided. This configuration brings about the following effect: At the catheter insertion, the catheter is deformed in such a way that the distal end portion of the second outer wall portion 116 bends into the inner cavity of the second lumen 112 from both sides of the second lumen slit 124. This brings about the following effect: At the insertion, the cross-sectional area of the body 101 at the second opening plane 122 becomes smaller, thereby providing the catheter with an excellent insertability.

Figure 30:
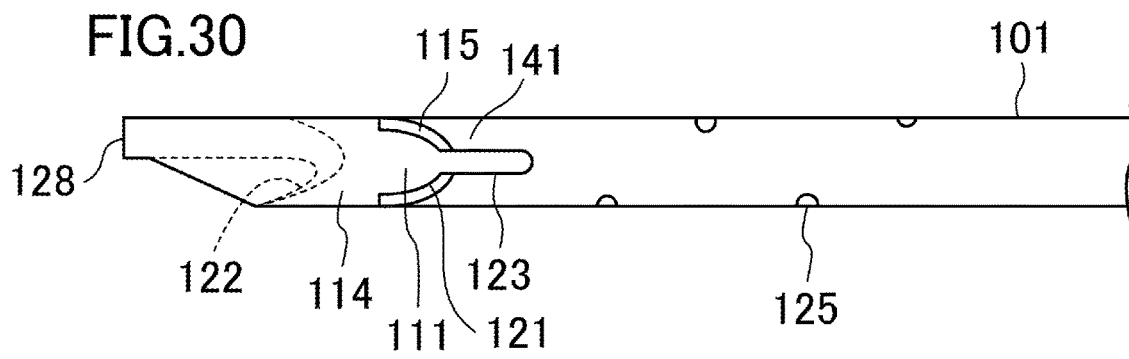
FIG. 30 is a top view of the multi-lumen catheter of a seventh variation.
Figure 31:
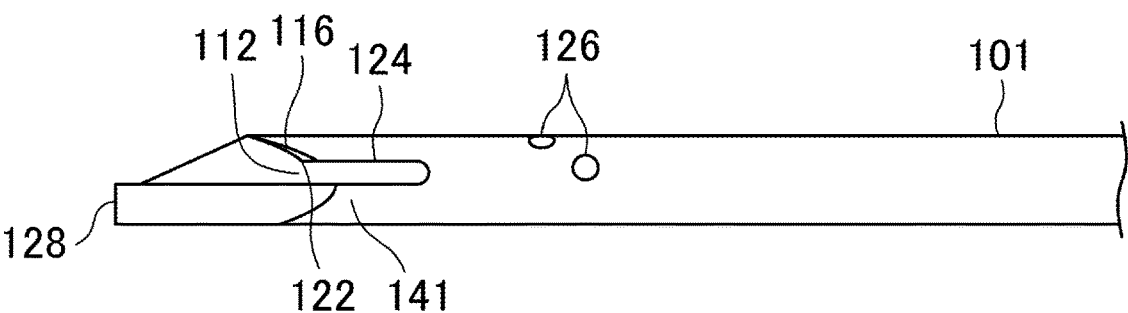
FIG. 31 is a bottom view of the multi-lumen catheter of the seventh variation.

According to a seventh variation, as illustrated in FIGS. 30 and 31, the inner space of the body 101 may be partitioned with the partition 114 into three lumens including the first lumen 111, the second lumen 112, and a third lumen. The third lumen may be used as a route for drug solution administration, central venous pressure measurement, or the like.

A third opening plane 128 at a distal end of the third lumen is provided more distally than the first opening plane 121 and the second opening plane 122, and positioned at the distal end of the body 101. This configuration allows for the following recirculation: The drug solution supplied into the blood vessel via the third lumen is sucked into the first lumen 111 immediately after the administration can be prevented during the forward connection. Moreover, with this configuration, the drug solution supplied via the third lumen is carried away from the first opening plane 121 with the flow of the blood returned via the second lumen 112 and the flow of the blood flowing through the blood vessel, thereby making it difficult for the recirculation to occur. Since the third opening plane 128 is positioned more distally than the second opening plane 122, the recirculation hardly occurs during the reverse connection as well.

The third lumen may have a smaller cross-sectional area than those of the first lumen 111 and the second lumen 112, for the sake of ensuring the blood flow rate of blood flowing through the first lumen 111 and the second lumen 112 and of the efficiency of the hemodialysis.

In the seventh variation, the first lumen slit 123 is provided at the distal end of the first outer wall portion 115 and the second lumen slit 124 is provided at the distal end of the second outer wall portion 116. Moreover, the flexible portion 141 includes the distal end portion of the first outer wall portion 115 where the first lumen slit 123 is provided, and the distal end portion of the second outer wall portion 116 where the second lumen slit 124 is provided.

This configuration brings about the following effect: At the catheter insertion, the catheter is deformed in such a way that the second outer wall portion 116 bends into the inner cavity of the second lumen 112 at the second opening plane 122 and the first outer wall portion 115 bends into the inner cavity of the first lumen 111 at the first opening plane 121. With this configuration, at the insertion, the cross-sectional area of the body 101 becomes smaller respectively at these opening planes, thereby attaining an excellent insertability of the catheter. According to the seventh variation, the flexible portion 141 may include a portion that ranges from the position of the proximal end of the first lumen slit 123 to the distal end of the body 101.

As in the present embodiment and each variation, the seventh variation may include the first lumen side pore(s) 125 and the second lumen side pore(s) 126. In the case where the seventh variation is configured such that the distal end portion of the second outer wall portion 116 includes the plurality of second lumen side pores 126, it is preferable that lines connecting either one of adjacent two second lumen side pores 126 and the center of the circle formed by the outer wall 113 form an angle in a range of 50° to 90°, for example. For other configurations than the configuration described above, the catheter of the seventh variation is not particularly limited.

Figure 32:
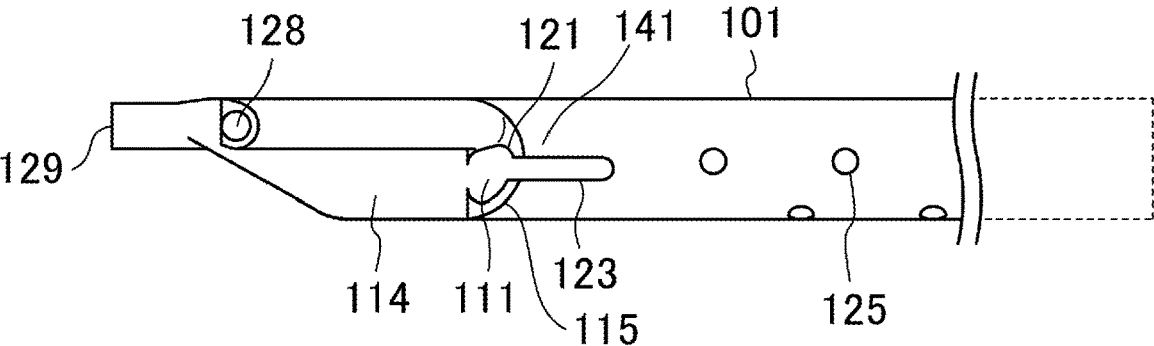
FIG. 32 is a top view of the multi-lumen catheter of an eighth variation.
Figure 33:
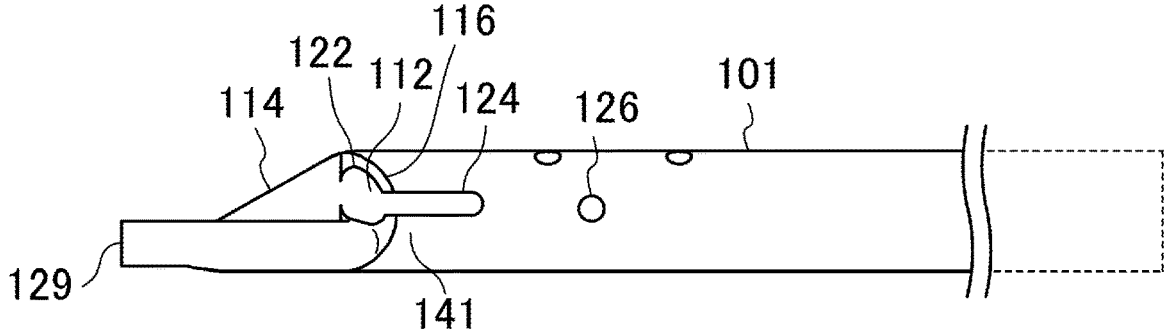
FIG. 33 is a bottom view of the multi-lumen catheter of the eighth variation.

According to an eighth variation, as illustrated in FIGS. 32 and 33, the inner space of the body 101 may be partitioned with the partition 114 into four lumens including the first lumen 111, the second lumen 112, the third lumen, and a fourth lumen. Like the third lumen, the fourth lumen may be used as a route for drug solution administration, central venous pressure measurement, or the like. In the eighth variation, providing two lumens in addition to the blood removal and blood return lumens, enables to eliminate the need for preparing a new route in case where a plurality of drug solutions is to be administered, thereby reducing the burden on an operator and the patient. The catheter may be configured to include more lumens.

A fourth opening plane 129 at a distal end of the fourth lumen is provided more distally than the first opening plane 121, the second opening plane 122, the third opening plane 128, and positioned at the distal end of the body 101. This configuration enables to prevent recirculation of the drug solution supplied into the blood vessel via the fourth lumen during the forward connection. This configuration enables to prevent recirculation of the drug solution supplied via the fourth lumen during the reverse connection.

The fourth lumen may have a smaller cross-sectional area than those of the first lumen 111 and the second lumen 112, for the sake of securing the blood flow rate of blood flowing through the first lumen 111 and the second lumen 112 and for the sake of the efficiency of the hemodialysis.

According to the eighth variation, the first lumen slit 123 is provided at the distal end of the first outer wall portion 115 and a second lumen slit 124 is provided at the distal end of the second outer wall portion 116. Moreover, the flexible portion 141 includes the distal end portion of the first outer wall portion 115 where the first lumen slit 123 is provided, and the distal end portion of the second outer wall portion 116 where the second lumen slit 124 is provided.

As in the seventh variation, this configuration can bring about the following effect: At the catheter insertion, the first outer wall portion 115 and the second outer wall portion 116 are deformed, thereby attaining an excellent insertability of the catheter. In the eighth variation, the flexible portion may include a portion that ranges from the position of the proximal end of the first lumen slit 123 to the distal end of the body 101.

As in the present embodiment and each variation, the eighth variation may include the first lumen side pore(s) 125 and the second lumen side pore(s) 126. In the case where the eight variation is configured such that the distal end portion of the first outer wall portion 115 includes the plurality of first lumen side pores 125, it is preferable that the lines connecting either one of adjacent two first lumen side pores 125 and the center of the circle formed by the outer wall 113 form an angle in a range of 50° to 90°, for example, and the same is applied in the configuration in which the plurality of second lumen side pores 126 is provided. Other than the configuration described above, the catheter of the eighth variation is not particularly limited.

The variations may be further modified as below.

For example, the second, third, and sixth to eighth variations including the second lumen slit 124 are not limited to the configurations above in which the flexible portion 141 includes, in addition to the distal end portion of the first outer wall portion 115, the distal end portion of the second outer wall portion 116. In these variations, it is sufficient that the flexible portion 141 includes at least the distal end portion of the first outer wall portion 115, so that the flexible portion 141 may not include the distal end portion of the distal end portion of the second outer wall portion 116. With the configuration in which the flexible portion 141 includes at least the distal end portion of the first outer wall portion 115, the distal end portion of the first outer wall portion 115, which has such a large outer diameter that would hinder the insertion, can be improved with a better insertability.

The catheters according to the variations may be configured such the proximal end of the body 101 is connectable with a branch pipe, a connector, or the like via a branch portion, as necessary.

The catheters of the present embodiment and the variation may be cuffed at a proximal location on the body 101 with a cuff made of synthetic fibers, as necessary, for the sake of preventing catheter-indwelling-induced infection during long-term indwelling.

INDUSTRIAL APPLICABILITY

The catheter according to the present disclosure is usefully applicable as a multi-lumen catheter with an excellent insertability.

DESCRIPTION OF REFERENCE CHARACTERS

101 Body
102 Branch Portion
103A Branch Pipe
103B Branch Pipe
111 First Lumen
112 Second Lumen
113 Outer Wall
114 Partition
115 First Outer Wall Portion
116 Second Outer Wall Portion
121 First Opening Plane
122 Second Opening Plane
123 First Lumen Slit
124 Second Lumen Slit
125 First Lumen Side Pore
126 Second Lumen Side Pore
128 Third Opening Plane
129 Fourth Opening Plane
131A Protection Cap
131B Protection Cap
132A Clamp
132B Clamp
141 Flexible Portion
142 Other Portion

The invention claimed is:

1. A multi-lumen catheter, comprising:
a body that is formed into a cylindrical shape and extends from a proximal end to a distal end and surrounded by an outer wall,
an inner space of the body being divided with a partition extending in a longitudinal direction, into a plurality of lumens including a first lumen and a second lumen,
the second lumen having a second opening plane at a distal end thereof, and the first lumen having a first opening plane at a distal end thereof, the second opening plane being positioned more distally than the first opening plane,
the outer wall including a first outer wall portion defining the first lumen and a second outer wall portion defining the second lumen,
the first outer wall portion having a first lumen slit notching a portion of a distal end of the first outer wall portion,
the body including a flexible portion having a lower hardness than other portions of the body, and the flexible portion including a distal end portion of the first outer wall portion where the first lumen slit is provided.

2. The multi-lumen catheter of claim 1, wherein
the first lumen slit is provided in a circumferential middle portion of the first outer wall portion.

3. The multi-lumen catheter of claim 2, wherein
the flexible portion includes a portion that ranges from the position of a proximal end of the first lumen slit to the distal end of the body.

4. The multi-lumen catheter of claim 2, wherein
the first outer wall portion has at least one first lumen side pore positioned more proximally than the first lumen slit.

5. The multi-lumen catheter of claim 2, wherein
the second outer wall portion has a second lumen slit notching a portion of a distal end of the second outer wall portion, and
the flexible portion includes a distal end portion of the second outer wall portion where the second lumen slit is provided.

6. The multi-lumen catheter of claim 2, wherein
the second outer wall portion has at least one second lumen side pore.

7. The multi-lumen catheter of claim 2, wherein
the first opening plane is inclined toward the proximal end with respect to the partition, and
the second opening plane is orthogonal to the partition.

8. The multi-lumen catheter of claim 2, wherein
the plurality of lumens includes three or more lumens.

9. The multi-lumen catheter of claim 2, wherein
the proximal end of the body is provided with branch pipes being connected respectively to the plurality of lumens and each having a connector at its proximal end.

10. The multi-lumen catheter of claim 1, wherein
the flexible portion includes a portion that ranges from the position of a proximal end of the first lumen slit to the distal end of the body.

11. The multi-lumen catheter of claim 10, wherein
the first outer wall portion has at least one first lumen side pore positioned more proximally than the first lumen slit.

12. The multi-lumen catheter of claim 10, wherein
the second outer wall portion has a second lumen slit notching a portion of a distal end of the second outer wall portion, and
the flexible portion includes a distal end portion of the second outer wall portion where the second lumen slit is provided.

13. The multi-lumen catheter of claim 10, wherein
the second outer wall portion has at least one second lumen side pore.

14. The multi-lumen catheter of claim 1, wherein
the first outer wall portion has at least one first lumen side pore positioned more proximally than the first lumen slit.

15. The multi-lumen catheter of claim 14, wherein
the second outer wall portion has a second lumen slit notching a portion of a distal end of the second outer wall portion, and
the flexible portion includes a distal end portion of the second outer wall portion where the second lumen slit is provided.

16. The multi-lumen catheter of claim 1, wherein the second outer wall portion has a second lumen slit notching a portion of a distal end of the second outer wall portion, and the flexible portion includes a distal end portion of the second outer wall portion where the second lumen slit is provided.

17. The multi-lumen catheter of claim 1, wherein the second outer wall portion has at least one second lumen side pore.

18. The multi-lumen catheter of claim 1, wherein the first opening plane is inclined toward the proximal end with respect to the partition, and the second opening plane is orthogonal to the partition.

19. The multi-lumen catheter of claim 1, wherein the plurality of lumens includes three or more lumens.

20. The multi-lumen catheter of claim 1, wherein the proximal end of the body is provided with branch pipes being connected respectively to the plurality of lumens and each having a connector at its proximal end.

* * * * *